United States Patent
Marterstock (10) Patent No.: US 11,491,266 B2
(45) Date of Patent: Nov. 8, 2022

(54) SAFE CONTROL OF DIALYSIS MACHINES USING A REMOTE CONTROL DEVICE

(71) Applicant: Fresenius Medical Care Deutschland GmbH, Bad Homburg (DE)

(72) Inventor: Stefan Konrad Marterstock, Dettelbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 641 days.

(21) Appl. No.: 16/551,199

(22) Filed: Aug. 26, 2019

(65) Prior Publication Data

US 2020/0086025 A1 Mar. 19, 2020

(30) Foreign Application Priority Data

Sep. 19, 2018 (DE) .......................... 102018123011.7

(51) Int. Cl.
    *A61M 1/16*     (2006.01)
    *G16H 40/67*     (2018.01)
    *G16H 20/40*     (2018.01)
    *A61M 1/28*     (2006.01)

(52) U.S. Cl.
    CPC .......... *A61M 1/1601* (2014.02); *G16H 40/67* (2018.01); *A61M 1/28* (2013.01); *A61M 2205/3327* (2013.01); *A61M 2205/50* (2013.01); *G16H 20/40* (2018.01)

(58) Field of Classification Search
CPC .................. A61M 1/1601; A61M 1/28; A61M 2205/3327; A61M 2205/50; A61M 2205/3553; A61M 1/14; G16H 40/67; G16H 20/40; G16H 40/63
See application file for complete search history.

(56) References Cited

U.S. PATENT DOCUMENTS

| | | | |
|---|---|---|---|
| 6,676,621 B1 | 1/2004 | Menninger | |
| 9,314,207 B2 | 4/2016 | Marterstock | |
| 2006/0143455 A1 | 6/2006 | Gitzinger | |
| 2007/0078678 A1* | 4/2007 | DiSilvestro | A61B 34/20 600/407 |
| 2009/0121865 A1 | 5/2009 | Hamel et al. | |
| 2009/0189988 A1 | 7/2009 | Jia et al. | |
| 2010/0318578 A1 | 12/2010 | Treu et al. | |

(Continued)

FOREIGN PATENT DOCUMENTS

| | | |
|---|---|---|
| DE | 10 2011 107 795 A1 | 1/2013 |
| DE | 10 2012 111523 A1 | 5/2014 |
| DE | 10 2016 105 199 A1 | 9/2017 |

OTHER PUBLICATIONS

International Patent Application No. PCT/EP2019/074345, Search Report (dated Nov. 26, 2019).

(Continued)

*Primary Examiner* — Kabir A Timory
(74) *Attorney, Agent, or Firm* — Leydig, Voit & Mayer, Ltd.

(57) ABSTRACT

A communication connection between a dialysis machine (such as a hemodialysis machine or a peritoneal dialysis machine) and a control device located away from the dialysis machine may be secured based on a safety protocol being implemented. The safety protocol may be executed in a server-side integrated circuit component and in a client-side integrated circuit component.

23 Claims, 6 Drawing Sheets

(56) References Cited

U.S. PATENT DOCUMENTS

2012/0226768 A1* 9/2012 Gaines .................. G16H 40/67
709/217
2016/0352701 A1 12/2016 Vora et al.
2019/0381230 A1* 12/2019 Biewer .................. G16H 40/63

OTHER PUBLICATIONS

German Patent Application No. 10 2018 123 011.7, Office Action (dated Jun. 28, 2019).

* cited by examiner

SAFE CONTROL OF DIALYSIS MACHINES USING A REMOTE CONTROL DEVICE

CROSS-REFERENCE TO RELATED APPLICATION

Priority is claimed to German Patent Application No. DE 102018123011.7, filed on Sep. 19, 2018, the entire disclosure of which is hereby incorporated by reference herein.

FIELD

The invention relates to the safe control of medical devices, such as dialysis machines, from a remote control device.

BACKGROUND

Dialysis machines are blood treatment devices which serve to deliver fluid of a patient to a fluid treatment component via a fluid pipe, where the fluid is treated by the fluid treatment component and is then returned to the patient via the fluid pipe which can be divided into an arterial and a venous branch. Examples of such blood treatment devices are hemodialysis machines. An example of a blood treatment device is described in U.S. Pat. No. 6,676,621, the disclosure of which is incorporated by reference herein in its entirety. Methods of hemodialysis, hemofiltration and hemodiafiltration are usually carried out with automatic hemodialysis machines. A plasmapheresis device serves to carry out a plasmapheresis, a blood treatment method during which the blood of the patient is separated into blood plasma and its corpuscular components (cells). The separated blood plasma is cleaned or substituted with a substitute solution and the cleaned blood plasma or the substitute solution is given back to the patient. Peritoneal dialysis machines serve for carrying out a peritoneal dialysis during which the abdominal wall of a patient is filled with a dialysis fluid via a catheter that is conducted through the abdominal wall, with the dialysis fluid having a concentration gradient of blood substances such as electrolytes (e.g., sodium, calcium and magnesium) as compared to the fluids produced naturally in the body. Via the peritoneum which serves as a membrane, toxic substances present in the body transgress from the blood vessels running in the peritoneum into the abdominal cavity. After several hours, the dialysis fluid in the abdominal cavity of the patient that is charged with the toxic substances that have transgressed from the body is replaced. Via osmotic processes, the water can transgress from the blood of the patient to the dialysis fluid via the peritoneum and can thus dehydrate the patient.

Dialysis machines are usually self-sufficient or self-contained, meaning the computer operation logic for controlling the machine is located on the machine itself. At least one user interface is implemented as an input and output unit on the dialysis machine.

In order to enhance flexibility, it is desirable that the control of the dialysis machines can be carried out on remote control devices as well.

The safety requirements for medical devices are considerably higher relative to other technical devices, and these safety requirements are also to be complied with for remote control in order to prevent misuse of to be protected data (e.g., protected health information (PHI) such as data relating to the patient) on the one hand, and on the other hand unintentional or unauthorized influence on the control of the medical device (e.g., via circuit-entering or intrusion on the control line).

SUMMARY

In an exemplary embodiment, the invention provides a control device for establishing a secure communication connection for controlling at least one medical device. The control device is remote from the at least one medical device. The control device includes: at least one control entity assigned to control the at least one medical device; a server-side communication device for communication with the at least one medical device; and an integrated circuit component configured to implement a protocol for establishing the secure communication connection for controlling the at least one medical device, wherein the protocol includes exchanging identification messages for one-to-one identification between a respective medical device and a respective control instance on the control device.

In another exemplary embodiment, the invention provides a medical device. The medical device includes: a client-side communication device configured for communication with a server-side communication device of a control device; and an integrated circuit component configured to implement a protocol for establishing a secure communication connection to the control device, and wherein the protocol includes exchanging messages with a respective control entity on the control device for one-to-one identification between the medical device and the respective control entity, wherein the respective control entity is configured for dedicated control of the medical device.

In yet another exemplary embodiment, the invention provides a medical system. The medical system includes: at least one medical device configured to communicate with a control device via at least one network; and the control device, wherein the control device is remote from the at least one medical device, and wherein the control device is configured to communicate with and control the at least one medical device via the at least one network; wherein the at least one medical device and the control device are configured to implement a protocol for establishing a secure communication connection between the at least one medical device and the control device, wherein the protocol includes a respective medical device exchanging messages with a respective control entity on the control device for one-to-one identification between the respective medical device and the respective control entity, wherein the respective control entity is configured for dedicated control of the respective medical device.

In yet another exemplary embodiment, the invention provides a method for establishing a secure communication connection between at least one medical device and a control device, wherein the control device comprises at least one control entity for controlling the at least one medical device. The method includes: the control device and the at least one medical device implementing a protocol for establishing a secure communication connection for controlling the at least one medical device, wherein the protocol includes a respective medical device exchanging messages with a respective control entity on the control device for one-to-one identification between the respective medical device and the respective control entity.

In yet another exemplary embodiment, the invention provides a server protection system for a control device which controls a remote medical device via a secure communication connection. The server protection system includes a check unit, which is configured to continuously check whether the secure communication connection is maintained and the treatment procedure is correct and, if so, instructs an enable unit. The server protection system further includes the enable unit, which sends an enable signal to the medical device when instructed by the check unit.

In yet another exemplary embodiment, the invention provides a client protection system for a medical device, which is controlled by a control device via a secure communication connection. The client protection system includes a monitoring unit, which is configured to continuously and automatically monitor whether at least one enable signal has been received within a predefined fault tolerance time and to provide an instruction for automatically transitioning the medical device to a safe device state.

In yet another exemplary embodiment, the invention provides an operating method for a distributed protection system including a client protection system on a medical device and a server protection system operating on a remote control device. In the operating method, it is continuously checked whether a secure communication connection between the medical device and the control device persists. The operating method includes automatically executed steps on the server protection system for signal exchange-based checking of whether a secure communication connection between the medical device and the control device persists and the treatment process is correct and, if so, cyclic transmission of at least one enable signal to the medical device. The operating method further includes automatically executing steps on the client protection system for fully automatic monitoring of whether the at least one enable signal was received within a predefined fault tolerance time and, if this is not the case, automatically transferring of the medical device to a secure device state.

In yet another exemplary embodiment, the invention provides a protection system for a medical device which is controlled by a remote control device. The protection system includes a server protection system and a client protection system. The protection system may be realized in a distributed matter.

BRIEF DESCRIPTION OF THE FIGURES

Exemplary embodiments of the present invention will be described in even greater detail below based on the exemplary figures. The invention is not limited to the exemplary embodiments. All features described and/or illustrated herein can be used alone or combined in different combinations in embodiments of the invention. Features and advantages of various embodiments of the present invention will become apparent by reading the following detailed description with reference to the attached drawings which illustrate the following.

DETAILED DESCRIPTION

Exemplary embodiments of the present invention provide for enhanced safety with respect to remote control of a medical device or a group of medical devices in manner that provides higher flexibility for control and maintenance on the one hand and that can conform on the other hand to the enhanced safety requirements associated with medical devices via structural constructional measures.

In the following, exemplary embodiments of the invention are described with respect to a device and a control device. Features, advantages or alternative embodiments mentioned therein are applicable to other embodiments and vice versa. In other words, the method-based embodiments can include features that are described and/or claimed in connection to the control device and vice versa. The respective functional features of the method are provided by respective structural modules, for example by electronic hardware modules or microprocessor modules of the system or the product and vice versa. That way, for example, the capturing of an initialization signal can be carried out via a respective signaling device which can, for example, be configured as a button on an interface.

According to a first aspect, the invention relates to a control device for the setup of a secured communication connection for controlling at least one remote medical device, such as a dialysis machine. The control device is thus arranged separately from or outside of the medical device and comprises at least one control entity and usually several control entities that are each assigned to controlling at least one medical device. For this purpose, the control device comprises:

- a communication device (on the side of the control device or the server) for communicating with the medical device; and
- an integrated circuit component which is configured to implement a link access protocol (or safety protocol) for creating a secured communication connection for controlling the medical device, and wherein the link access protocol exchanges identification messages for the one-to-one identification of the medical device and the one-to-one identification of the respective control entity on the control device.

In an exemplary embodiment, the carrying out of the link access protocol is initiated by determining an initiation message on the control device. The initiation message is usually sent to the control device by the medical device. Thus, the initiation of the method for building a secured communication connection comes from the medical device, and the sovereignty on the control situation lies with the to be controlled medical device. This way, security can be enhanced by preventing remotely triggered compromise attempts.

In an exemplary embodiment, the control device comprises a user interface. The user interface serves to determine control signals to control the medical device. The user interface can cumulatively or alternatively serve not only for data entry (of control signals), but also for data output of state data of the medical device. This way, a device and/or treatment state can be issued. It can, for example, be an interface directly built in on the control device, such as a graphic interface. Alternatively, it is possible to implement the user interface on a separate device and not on the control device. This way, the flexibility for device interconnection for establishing a secured communication channel can be enhanced. In this case, the separate user interface is in data exchange with the control device.

In another aspect, a medical device is controlled via a remote control device. The medical device comprises a communication device on the side of the client which is configured for data exchange with a communication device on the side of the server of the control device. Furthermore, it comprises an integrated circuit component which is configured to implement a link access protocol for establishing a secured communication connection to the control device and wherein the link access protocol exchanges identification messages for one-to-one identification of the medical device and one-to-one identification of the respective control entity on the control device, wherein each control entity is configured for the dedicated control of a respective medical device.

In another aspect, a control system for establishing a secured communication connection controls at least one medical device, such as a dialysis machine, with a remote control device. The control system comprises:
 the medical device that is to be controlled; and
 a control device as described above wherein the involved devices are in data exchange via at least one network (wireless and/or wired).

In an exemplary embodiment, the control system can comprise additionally optionally a user interface that can either be implemented on the control device or externally and separately or separated from it, for example on a mobile communication unit such as a mobile radio unit or another electronic device or end device. Therein, the separate device with the user interface is in bidirectional data exchange with the control device and/or with the control system. With that, flexibility can be enhanced. In an advantageous embodiment it is ensured that the external user interface can only communicate with the control device via the medical device if the external user interface is in the spatial field or close to the medical device. This can, for example, be carried out via a position determination, such as described in U.S. Pat. No. 9,314,207, which is incorporated by reference herein in its entirety. This way, non-authorized access via radio networks is further hindered.

In another aspect, a backup procedure is provided for at least one medical device, such as a dialysis machine. The backup procedure serves to establish a secured communication connection between the medical device and a remotely arranged control device, wherein the control device comprises at least one control entity which is each assigned to control at least one medical device. The backup procedure comprises first stages that are carried out on the medical device and second stages that are carried out on the control device. Both stages together build a distributed procedure for carrying out a link access protocol on the control device and the medical device for establishing a secured communication connection for the (later) control of the medical device. The link access protocol exchanges identification messages for one-to-one identification of the medical device and one-to-one identification of the respective control entity on the control device with the medical device.

In an advantageous embodiment of the invention, the backup procedure can additionally comprise before execution the procedural step:
 determining a trigger signal on the medical device to trigger the execution of the link access protocol (thus, it is ensured that the initiation of the interconnection process comes from the medical device, which enhances safety).

In an advantageous embodiment of the invention, the execution of the link access protocol comprises the following steps:
 sending an initiation message with a distinct device identification for the medical device from the medical device to the control device and especially to all control entities on the control device (if several control devices are used in the system, the initiation message can also be sent to all control devices, for example, as a broadcast message);
 receiving the initiation message on the control device;
 from the control device: sending a first acknowledgement message to the medical device with an identification of the assigned control entity as an answer to the received initiation message;
 receiving the first acknowledgement message on the medical device; and
 from the medical device: sending a second acknowledgement message as an answer to the received first acknowledgement message to the control device.

In an advantageous embodiment of the invention, the control device is configured after receiving the initiation message as an answer to the received initiation message. The configuration can comprise, for example, the determination of a specific control entity for the respective medical device and thus its allocation process to the device. The configuration can comprise the determination of parameters (parameterizing for the specific medical device). This is especially advantageous if the control device is to control several medical devices or if several secured communication connections are to be established between the control device and different medical devices. This way, the technical advantage can be achieved that several medical devices can be operated and controlled in parallel or simultaneously via a respective network connection. Consecutively, the central and uniform control of a group of devices (e.g., by using a pre-configurable control scheme stored in a database) is simplified.

In other words, several control entities (for several medical devices) can be implemented on the control device. Preferably, the initiation message is then a broadcast message to all control entities of the control device. Alternatively or cumulatively, several control devices can be integrated in the same network.

In another advantageous embodiment of the invention, the initiation message comprises an equipment code which represents the technical equipment of the medical device. The term equipment relates to the technical equipment of the device and can comprise the following parameters: a version of the device, implemented hardware and/or software, modules of the device and/or intended use and/or performance data of the device and further technical parameters. Alternatively or cumulatively, the initiation message can also comprise calibration data.

In another advantageous embodiment of the invention, an interconnection result (coupling result) is shown on a user interface of the control device and/or the medical device after the execution of the link access protocol. The interconnection result can identify an indication towards the success of the backup procedure or of the interconnection process. The interconnection result can be implemented in the form of a message, for example, in order to signal that the secured pairing was successful or failed.

In another advantageous embodiment of the invention, an interconnection result is signaled via an activation of a hardware component after the execution of the link access protocol. The hardware component can be configured to represent at least two states in parallel: a first state of a successful interconnection and a second state of a defective or unsuccessful interconnection. This can take place in the form of a signal light signaling (e.g., in the form of an electronic signal light: green for successful interconnection and establishing of a secured communication channel and red for a failed interconnection).

In another advantageous embodiment of the invention, the execution of the link access protocol comprises:

- from the control device: evaluating whether a second acknowledgement message has been received as an answer to a received first acknowledgment message on the control device within a predefined timeout time phase and if this is not the case: issuing a failed interconnection message at least on the control device (and/or on further electronic entities, such as on the medical device) and/or if this is the case: issuing an interconnection message (that signals a successful result) on the control device; and
- in the case of a successful result, the establishing of a secured communication connection can be carried out (and after the secured communication connection is established, the medical device can be operated by remote control in a secured way from the control device).

According to another aspect, a server protection system is provided for a control device which controls a remote medical device, such as a dialysis machine, via a secured communication connection. The server protection system comprises a test unit and a release unit. The test unit is configured to carry out a two-way check, namely, continuously checking that the secure communication connection persists and the treatment procedure is correct so that there is no patient health condition and if so (i.e., if the secure communication connection persists and if the treatment flow is correct on dialysis machine), the release unit is instructed with at least one command mentioned below. Checking whether the treatment procedure is correct is preferably carried out via a checking algorithm on the basis of the data exchanged via the secure communication connection. Testing checks the procedure on the dialysis machine for correctness. A first aspect of testing thus relates to the correctness of the communication (data integrity) and a second aspect relates to the examination of the data content itself (e.g., temperature below threshold). In both cases, a release signal would be omitted if one of the two tests failed. In an advantageous embodiment of the invention, the test algorithm can be executed exclusively on the medical device. Thus, the security can be increased. The release unit sends an enable signal to the medical device when instructed by the test unit or initiates the dispatch of the enable signal by another electronic unit.

According to a further aspect, a client protection system is provided for a medical device, such as a dialysis machine, which is controlled by a control device via a secure communication connection. The client protection system comprises a monitoring unit and transfer logic. The monitoring unit is configured to continuously and automatically monitor whether the at least one enable signal has been received within a predefined fault tolerance time. Optionally, a second aspect may be monitored in addition, namely, whether the treatment flow is correct, and if the two-aspect monitoring was unsuccessful in at least one aspect, instruct a transfer logic with a corresponding command (described as follows). The transfer logic is configured to automatically transition the medical device to a secure device state when instructed by the monitoring device according to the result of the monitoring, for example, via an omitted further release signal of the monitoring unit in a good case or via a blocking signal in case of bad monitoring (i.e., if at least one of the aspects does not indicate a successful state).

The transfer logic is an electronic module (hardware and/or software) that is implemented on the medical device and moves the device from an operating state to a safe device state and vice versa. In a figurative sense, the transfer logic thus acts as a switch. The transfer logic is controlled by corresponding input signals, such as a blocking signal or a further enable signal. The safe state of the device is characterized by the fact that no measures that endanger patient safety can be triggered. In a special case, the medical device may also be partially or completely disabled if it is to be transferred to the secure device state. In an exemplary embodiment, it is possible to configure in advance which functionalities should be able to be operated or executed in the safe device state (for example stopping blood flow to the patient). Thus, the arterial and venous clamps are usually closed to the patient, thus ensuring that no energy and/or fluid transport between the dialysis machine and the patient is possible anymore. In other cases, it may also be configured to stop the blood pump or shut down the dialysis machine (for example, if the internal electrical voltages are too high). There are other cases in which, for example, a blood return is allowed.

In an exemplary embodiment, it is provided in the client protection system that the monitoring unit instructs the medical device or another electronic entity on the medical device (e.g., a transmitting unit and/or the client-side communication device) to send status data packets via the secure communication connection to the server protection system if at least one enable signal was received within a predefined fault tolerance time.

According to another aspect, an operating method is provided for a distributed protection system comprising a client protection system implemented on a medical device, such as a dialysis machine, and further comprising a server protection system that can be implemented on a control device remote from the medical device and in which it is continuously checked whether a secure communication connection between the medical device and the control device persists. The method comprises the following, automatically executed steps:

- on the server protection system: signal exchange-based check whether a secure communication connection between the medical device and the control device persists and the treatment process is correct or if there is no patient endangerment state and if the check was successful (secure communication connection continues and the treatment process is correct or there is no patient endangerment state): cyclic transmission of at least one enable signal to the medical device; and
- on the part of the client protection system: fully automatic, computer-implemented monitoring of whether the at least one release signal was received within a predefined fault tolerance time and, if this is not the case: automatic transfer of the medical device to a secure device state.

In an exemplary embodiment, the signal exchange-based checking may be performed by the medical device cyclically sending status data packets to the protection system and the protection system analyzing the consecutively correct receipt of the status data packets. This has the technical advantage that the data packets to be transmitted anyway, such as sensor data or status data can be used to form the basis of a server-side audit.

In a further advantageous embodiment of the operating method according to the invention, the status data packets may include a time stamp or a sequence number (as a consecutive number). This is particularly helpful if the data packets would otherwise be indistinguishable in terms of their time signal.

In a further advantageous embodiment of the operating method, the server protection system can be implemented on the control device, preferably in a protected memory area of the control device. As an alternative, the server protection system can also be implemented on a hardware control unit separately implemented on a second control device. This can improve safety.

In a further advantageous embodiment of the operating method, the same is implemented completely automatically and computer-implemented and without user interaction. Thus, the operation of the protection system can be made safer by excluding incorrect entries of a user.

According to another aspect of the invention, a protection system is provided in a distributed manner for a medical device, such as a dialysis machine, which is controlled by a remote control device. The protection system comprises:
 a server protection system as described above; and
 a client protection system as described above.

A first section of the method of operation may be performed on the control device and a second section may be performed on the medical device. The second section can also be implemented on a separate entity, such as a protection system. It is also possible that the protection system is at least partially implemented on the control device. To ensure safety, part of the protection system should be implemented in the dialysis machine, including at least one component that operates in the manner of a "watchdog" or a monitoring unit.

In an exemplary embodiment, in the operating method, the testing (whether the at least one enable signal was validly received) may be performed by the medical device sending status data packets to the protection system cyclically and/or in an event based manner (i.e., after predefinable events) and the protection system monitoring the consecutive correct receipt of the status data packets. "Consecutively correct" in this context means that a sequence of electronic messages, namely the status data packets, is monitored. The sent sequence should correspond to the received sequence. Once a difference is detected (e.g., if the sequence being sent is 1-3-5-7- . . . , and the sequence received is 1-5-3-7-), then the check procedure or check yields an error, though in the end, all status data packets could be received. This leaves, for example, the assumption that the network connection was interrupted for a short time and in particular during the transmission process of packet 5 and that the transmission of the data packet 5 was made up at a later time.

In an exemplary embodiment of the operating method, the status data packets may include a time stamp. Thus, the quality of the check as to whether an enable signal has been present, and in particular whether the enable signal was valid, can be improved by checking not only the sequence (sequence of signals) but also their timestamps. The timestamps may represent a continuous sequence. For example, for a 1 minute grid, the sequence could be: minute 1, minute 2, minute 3, minute 4, etc. if it is detected that the timestamp 1 has been detected at 3, this is an indication that the sequence was interrupted and indicates a (possibly) temporary interruption of the secured communication channel. This intermediate result can be output on the user interface.

In an exemplary embodiment of the operating method, the protection system can be implemented on the control device, preferably in a protected memory area. Alternatively, the protection system can be connected as a separate electronic module (hardware and/or software module) via a corresponding data connection with the control device and integrated into the system in addition to the same.

According to another aspect, a protection system, realized in a distributed manner, is provided for a medical device, such as a dialysis machine, which is controlled by a remote control device. The protection system is operated according to method described above. In this case, the user interface of the control device can be connected as an external (e.g., mobile) entity.

Basically, and to comply with safety requirements, a dialysis machine accepts only one control entity and one protection system entity. By using the trigger signal it is ensured that the interconnection between the dialysis machine and the control device, thus the establishment of the secure communication connection is only possible outside a medical treatment (dialysis treatment). The monitoring unit can also be used to ensure that it is not possible to switch to pairing-mode during a treatment by blocking such switching.

The first acknowledgement message that the control entity sends to the medical device is preferably encrypted. This can be done with the help of a "secret" provided by the manufacturer of the device. For example, in the first acknowledgement message, the dialysis machine expects a check number, which is determined by the control entity on the basis of the secret and the medical device identification number to be assigned. Thus, it can also be ensured that the medical device only accepts the acknowledgement messages meant for itself and not those of the neighboring device. The processing of acknowledgement messages from unauthorized instances/hackers is thus prevented.

However, the secret does not necessarily have to be implemented at the factory, but can also be configured, for example, by a service technician via interaction. For example, the secret may be downloaded via software download or pluggable hardware on the medical device and also imported by the service technician in the control unit or manually entered (e.g., keyboard, voice). As a result, a greater variety in the secrets is possible. It is also possible for one of several predefined secrets to be stored in the medical device at the factory, but the service technician should set, configure or completely or partially enter this on the control device.

It can be preconfigured that a trigger signal can only be triggered by an operation of an authorized person of staff in order to further increase the safety.

During the establishment of the secure communication connection (pairing process) preferably broadcast messages are used. The broadcast messages contain the respective interconnection partners, so that all network participants are informed, whether they were accepted to establish the secure communication connection or not and which device is the pairing partner. By displaying the interconnection result while displaying the associated device identification number, for example, authorized personnel (service technician) can again check the correctness of the process at the end. This increases security and transparency. Once the encryption is active (from the first acknowledgment message, the other participants notice this and can issue a corresponding message), from then on unicast messages are used.

The device identification number from the initiation message can already be displayed to the service technician at the beginning on the user interface of the control device in order to be able to abort an incorrect pairing process at an early stage.

The network may be a private network, such as a physically independent clinic network. In particular, it may be a wired network or a radio network with a limited radio range.

In an embodiment of the invention, it is provided that calibration data in the device, for example, can also be transmitted from the medical device to the control device at the end of the interconnection process or during the instantiation of the control entity.

The control device may be an electronic terminal with a processor or microprocessor that executes an application for controlling the medical device. The control device may be adapted directly or indirectly with a user interface. "Indirectly" in this context means that the user interface may also be embodied on an external device (e.g., a mobile device) that is in communication with the control device through a corresponding network connection (e.g., wireless local area network (WLAN)) or interface. The control device can be configured as a server. The control device can be implemented as a physical and/or virtual server and can be operated by an operating system. The control device can be configured for (central) control of a plurality of medical devices. The control device can be configured for this purpose with at least one control entity. The control entity can be an application intended to control a specific medical device. The association between the control entity and the medical device to be controlled is distinct. In other words, a medical device is controlled by exactly one control entity. This serves to meet the increased safety requirements.

A secure communication connection is to be established between the control device and the to be controlled medical device. This means that the communication channel is additionally secured. This is achieved by storing a predefined data exchange protocol with messages to be exchanged and verifying that the data exchange protocol has adhered to the sequence of predefined messages (as per the protocol). Control commands to the medical device and/or status data to the control unit can be transmitted via the secure communication connection between the control device and the medical device to be controlled. The secured communication connection can thus be configured preferably for bidirectional data exchange.

The medical device can be an electronic device that provides medical functions. It can be a dialysis machine or another blood treatment device.

In order to provide any data exchange between the control device and the medical device, the control device is configured with a communication device for preferably wired communication with the medical device. The communication device located on the control device is also referred to as a server-side communication device. In correspondence thereto, each medical device also has a communication device, which may be referred to as a client-side communication device.

In an exemplary embodiment, the control system comprises not only the medical device and the control device, but additionally a third electronic device, which acts more or less as a mobile user interface of a terminal for the control device. Thus, the flexibility of operation can still be increased, However, in order to be able to ensure the security, it is to be detected automatically on the control device when the third mobile user interface device approaches. Therefore, in an exemplary embodiment of the invention, it is provided that the medical device detects a spatial approximation of the mobile terminal (user interface), a communication device or another component of the control device (and additionally indicates which device it is with an indication of a unique address). For this purpose, methods may be used as described in U.S. Pat. No. 9,314,207, the disclosure of which is hereby incorporated by reference herein in its entirety. This makes it possible, for example, to additionally secure smartphones or tablets as a mobile user interface via a local location. Interconnection or pairing is, for example, only possible if the mobile operator interface (mobile phone/smartphone/tablet) is within a pre-configurable number of meters of the dialysis machine. This additional protection via position detection can also be applied in another embodiment of the invention, for example, as an additional function for pairing with a dialysis machine, without the use of a control device.

The server-side and client-side communication devices exchange data over at least one network (e.g., local access network (LAN), WLAN, near-field communications such as Bluetooth, dedicated short range communication (DSRC), or even wired communications) to execute the safety protocol.

The integrated circuit component is configured to implement a security protocol for establishing the secure communication connection for controlling the medical device. The integrated circuit component can be provided as a processor, microprocessor, controller or other hardware component. For this purpose, it can include a server-side and a client-side component. Accordingly, a first section of a computer program for executing the safety protocol is formed on the server-side integrated circuit device of the control device. The corresponding analog unit resides as a client-side integrated circuit component on the medical device, on which a second section of the computer program for executing the safety protocol is implemented.

The link access (safety) protocol is used to identify the medical device in a one-to-one manner and to identify the respective control entity on the control device in a one-to-one manner. After the correct execution of the safety protocol, it can advantageously be ensured that it is determined on the medical device from which control device or which control instance it is controlled, and vice versa, it is determined on the control device which medical device is to be controlled. If, for example, control signals of other devices are received on the medical device, these are inadmissible, and it can be ruled out immediately that they can be used for control. The safety protocol is fully computer implemented and runs automatically.

In another embodiment, after the establishment of the secure communication connection or after the execution of the safety protocol, an encryption method can be activated in order to additionally secure the secure communication connection (i.e., virtually twice). This makes it possible that the assumption of "foreign" (i.e., not allowed) control and/or status data packets can be safely excluded by encryption. Thus, the security can be further improved.

Identification messages are electronic data packets that are exchanged between the medical device and the control device. In an exemplary embodiment, these comprise at least one initiation message and/or at least one first acknowledgement message and/or at least one second acknowledgement message. Alternatively and optionally, the identification messages may include status information (e.g., sensor data, device status data, version number of hardware and/or software, etc.).

The initiation message is an electronic message. It serves as a first step to initiate safety protocol execution. The initiation message is generated locally on the medical device. The initiation message may include a unique device identification of the medical device. Optionally, further data fields may be included in the initiation message, for example, a timestamp, configuration data, etc. The initiation message is sent from the medical device to the controller(s). The safety protocol can only be executed if the initiation message was generated correctly and could be received correctly on the controller.

The trigger signal is an electronic signal. It is used to trigger the execution of the safety protocol and precedes the generation of the initiation message. In an exemplary embodiment, the initiation message is generated only if the trigger signal could be detected. The trigger signal is recorded locally on the medical device. It may be pre-set that the trigger signal is requested actively (e.g., in the form of an output on the user interface). Furthermore, it can be pre-set that, if the trigger signal is incorrectly input or missing, the same is again requested repeatedly and/or otherwise a corresponding output is generated (for example in the sense of "Trigger signal not detected→secured communication connection cannot be established"). The trigger signal can increase the security of the method by implementing, as it were, a second security level (1st security level: detecting the trigger signal-2nd security level: generating and sending the initiation message), which is monitored for compliance. The trigger signal can take place via the input of a predefined user signal, which is sometimes detected on an initiation module which is formed locally on the medical device. The initiation device may be configured as a button on a (e.g., graphical) user interface or as a button and/or switch on the medical device. The initiation message is sent from the medical device to the controller. Moreover, it is provided in an advantageous variant of the invention that the trigger signal does not have to be explicitly entered by the user, but it can be generated and triggered automatically indirectly from a device state. So, for example, it can be provided that the trigger signal is generated automatically the first time the medical device is started and/or in the context of a commissioning procedure and/or due to other preconfigured events.

The control signals detected on the control device are used for (remote) control of the medical device. The control signals can be generated automatically. The control signals can also be generated directly from user inputs of a user. Alternatively or cumulatively, the control signals can also be calculated on the basis of the recorded user inputs. The control signals may consist of a single command (e.g., enable/disable the medical device) or a sequence of commands (first instruction, second instruction, . . . nth instruction to be executed and driven on the medical device).

The interconnection result is an electronic message that is automatically generated. The interconnection result can be implemented differently depending on the embodiment of the invention. In the simplest case, it is a message (secure pairing successful: pairing message and/or secure pairing unsuccessful: mis-pairing message). Alternatively, further data fields may be formed in the interconnection result, for example, a timestamp indicating the beginning of the established secure communication channel. Alternatively, the secure communication channel can be configured with an expiration (e.g., an expiration time or date), so that the secured communication channel is automatically deleted or reduced again after a predefined period of time. The interconnection result may also include further metadata. The interconnection result can be output via a hardware component configured for this purpose. The hardware component can, for example, be a signal light circuit (green signal for successful setup and red signal for failed setup). In addition to the colorization based signaling described above, acoustic signaling may be provided. Alternatively or cumulatively, a third (e.g., orange) signal may be provided to signal that, at the moment, the safety protocol is being executed to establish the secure communication connection After the secure communication channel has been established, it is provided according to a further aspect of the invention that the continuity of the secure communication connection is continuously checked. This can further increase the security of the distributed system. It is therefore also immediately recognized that a secure communication connection could be successfully established, but this no longer exists after a certain time or is interrupted (for example, in the case of a temporary network failure). In the prior state of the art, safety could not be ensured in such cases because the device could not execute the control signals in the interruption period, but executes the sequence of the next control signals after the end of the interruption as planned. Thus, the absence of the previous control signals is difficult or impossible to detect. This can result in an erroneous control of the medical device. According to one aspect of this application, this can be safely excluded by continuously and automatically monitoring the continuity of the (once) established secure communication connection.

The checking may take place continuously. The checking can be carried out according to a predefined time pattern and/or following the receipt of new telegrams/data packets. It can thus be defined in a configuration phase that the check is triggered automatically after a time interval has expired. Likewise and/or cumulatively, the checking can be triggered on an event-based basis (e.g., after detection of an input signal on the medical device, after the detection and before the execution of certain (e.g., particularly safety-relevant) control commands, after a restart of the medical device and/or the control device or after other events). The checking takes place in a signal-based manner. In other words, the checking is preferably carried out automatically and without user interaction. Thus, the safety of the operating and control method is increased. The checking takes place at least within the predetermined error tolerance time.

The enable signal may not be a simple one-bit signal that is sent to the medical device via the secure communication connection. The enable signal should be coded safely. "Safe" in this context means that a corruption by the signal transmission and/or signal processing with high probability does not lead to a false positive interpretation by the dialysis machine. It is conceivable to use a codeword from a large number of numbers or, when using a 1-bit signal, the additional use of suitable checksums. This serves to ensure that the reception of the enable signal can be monitored on the medical device. For this purpose, a protocol may be defined in advance, which can, for example, determine that the enable signal has been received within a certain time interval and/or within a predefinable fault tolerance time and/or in a predefinable quality (e.g., with a correct checksum).

The safety method and the operating method can be provided as a computer program, such as a microprocessor program.

In another exemplary embodiment, the invention provides a computer program product which is loaded or loadable in a memory of a computer or an electronic or medical device with a computer program for carrying out the security method and/or operating method described above, if the computer program on the computer or the electronic computer or medical device is executed.

In another exemplary embodiment, the invention provides a computer program for carrying out the method described above when the computer program is executed on a computer, an electronic or medical device. It is also possible that the computer program is stored on a medium readable for the computer or the electronic or medical device.

In another exemplary embodiment, the invention provides a data protocol, which is implemented according to the safety protocol described above. The data protocol is characterized by the exchange of identification messages, which according to an exemplary embodiment of the invention comprise an initiation message and first and second acknowledgement messages.

In the following detailed description, exemplary embodiments and their features and further advantages are described in connection with the figures.

In the following, the invention is described in greater detail in connection to the figures via examples of embodiments.

Figure 1:
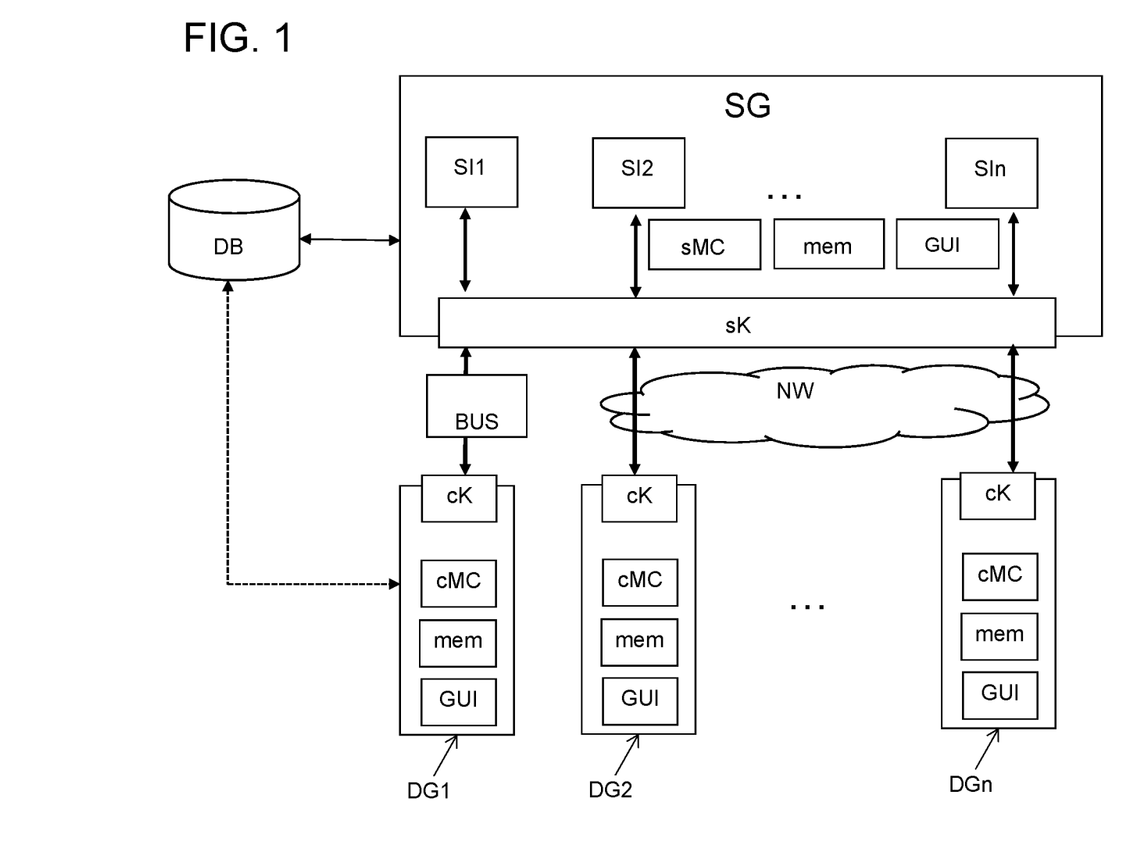
FIG. 1 shows a schematic representation of a group of dialysis machines which are controlled by a control device according to an exemplary embodiment of the invention.

FIG. 1 shows dialysis machines as an example of medical devices that are to be controlled by a control device SG only when a secure communication connection has been established.

As shown schematically in FIG. 1, a dialysis machine can be operated in a group of several dialysis machines and controlled centrally by a control device, the latter being, for example, configured as a control server. For this purpose, a plurality of control entities are formed on the server acting as the control device SG, each of which is assigned to exactly one respective dialysis machine to be controlled. In FIG. 1, 1 to n control entities SI1, SI2, . . . SIn are provided by way of example for 1 to n dialysis machines DG1, DG2, . . . DGn. The dialysis machines may be connected to the control device SG via different networks, e.g., via a bus system or via a wireless network NW for digital data exchange.

To establish a secure communication connection, each dialysis machine comprises a client-side communication device cK, which is intended to communicate with a server-side communication device sK for this purpose. Furthermore, a client-side integrated circuit component cMC may be formed on each dialysis machine, as well as a memory mem and a user interface GUI, which can, for example, be a graphical user interface.

The control device SG comprises a plurality of control entities, wherein a first control entity SI1 is assigned to a first dialysis machine DG1, a second control entity SI2 to a second dialysis machine DG2, etc. For communication, the control device SG includes the server-side communication device. In addition, the server-side integrated circuit component sMC and optionally a memory mem and optionally a user interface GUI are formed on the control device SG.

Figure 4:
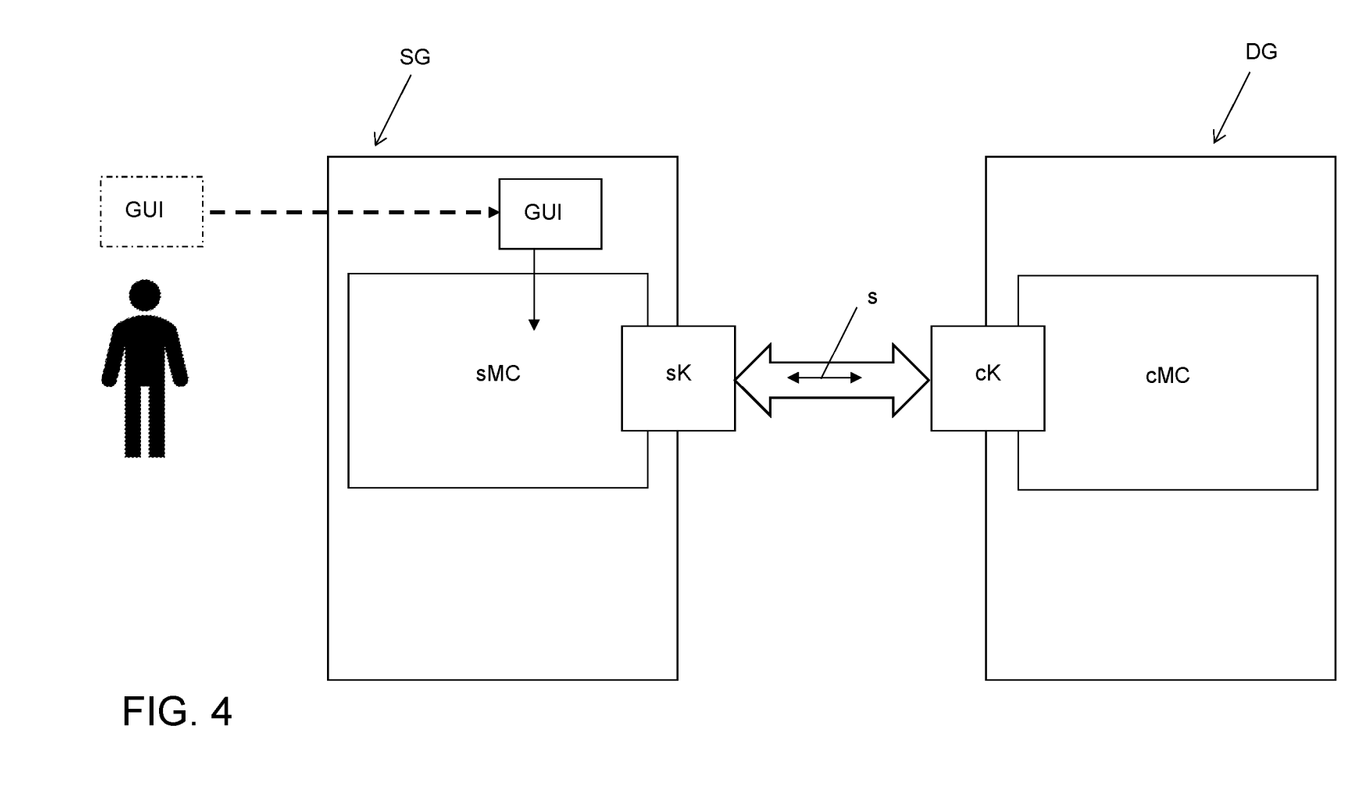
FIG. 4 is a block diagram showing a representation of electronic modules for establishing a secured communication connection between a control device and a dialysis machine according to an exemplary embodiment of the invention.

The user interface can be cumulatively or alternatively formed on an external device in an alternative embodiment of the invention, which is connected to and in communication with the control device SG. This is indicated in FIG. 4 in that the user interface GUI (shown with dashed lines) can also be provided separately and externally of the control device. Then, additional protection techniques are preferably employed, for example via the position location of the mobile interface device, which should act as user interface GUI.

As indicated in FIG. 1, the control device SG can be in data exchange with a database DB. There, for example, rules for the formation of the safety protocol can be developed and deposited, which can be changed independently of the dialysis machines and the control unit SG. Optionally, a dialysis machine or selected or all dialysis machines can be connected to the database DB, for example, to be able to access configurations and rules.

Figure 2:
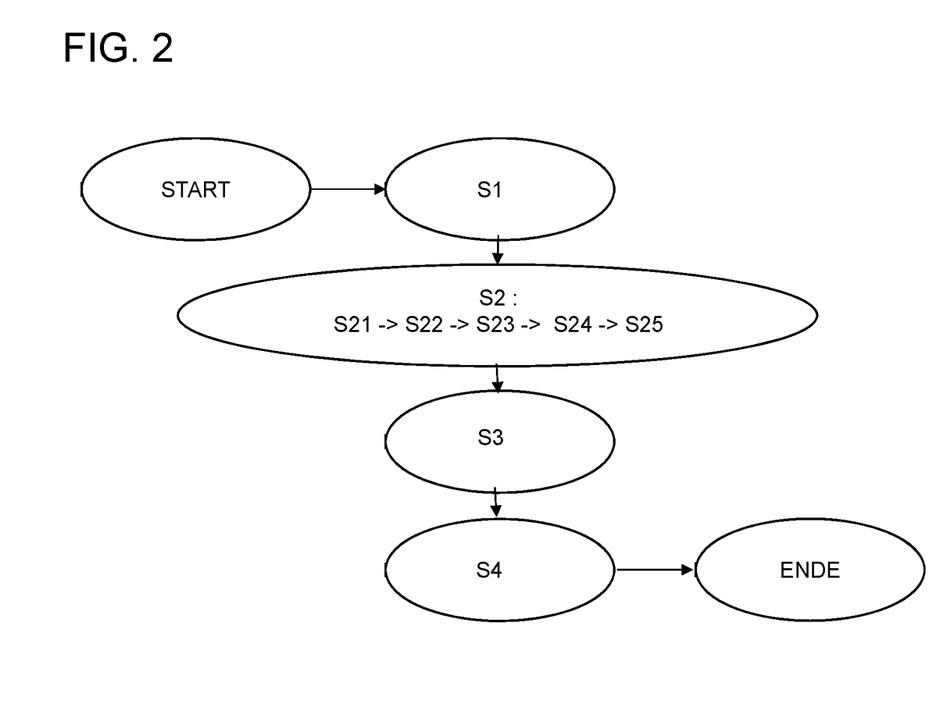
FIG. 2 is a flowchart for a security method for establishing a communication connection for the secure remote control of a dialysis machine according to an exemplary embodiment of the invention.
Figure 3:
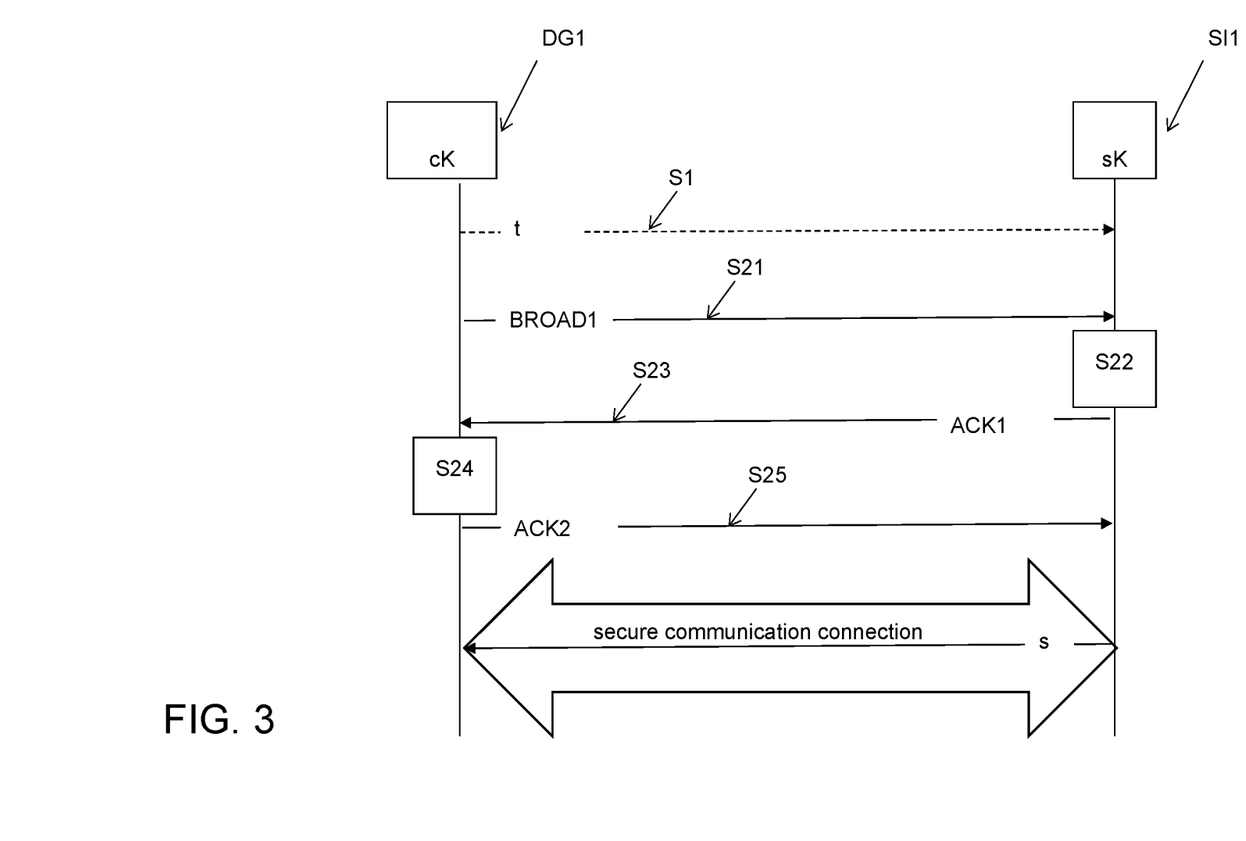
FIG. 3 is an interaction diagram showing a data exchange of signals and messages between the control device with its control entities and a dialysis machine according to an exemplary embodiment of the invention.

The establishment of the secure connection is triggered and/or initiated locally by a dialysis machine. For this purpose, (optionally)—as shown in FIG. 2 and FIG. 3—in a first step S1 a trigger signal t can be detected on the dialysis machine in order to trigger the establishment of the secure communication connection and the execution of the safety protocol in step S2. The execution of the safety protocol S2 preferably comprises the following steps:

- sending S21 an initiation message BROADC1 with a unique device identification for the medical device from the medical device to the control device SG;
- receiving S22 the initiation message BROADC1 on the control device SG;
- on the part of the control device SG: sending S23 a first acknowledgment message ACK1 to the medical device with an identification of the associated control entity in response to the initiation message;
- receiving S24 of the first acknowledgment message ACK1 on the medical device and
- on the part of the medical device: sending S25 a second acknowledgment message ACK2 in response to the received first acknowledgment message ACK1 to the control device SG.

Optionally, during or before step S22, a configuration of the respective control entity can be executed. In particular, however, after step S22, a configuration is made based on the data received with the initiation message BROADC1. This is sometimes useful when the initiation message BROADC1 contains configuration data of the medical device (e.g., version number, equipment code, and the like). Furthermore, such an automatism can be implemented, which automatically generates or applies new, required server instances if required.

FIG. 3 shows an interaction diagram between the client-side communication device cK on the dialysis machine DG1 and the server-side communication device sK on the first control entity SI1 of the control device SG. First, the trigger signal t is detected on the dialysis machine DG1 and then sent to the first control entity SI1. The trigger signal is needed to put the dialysis machine DG1 in the pairing mode. Without this trigger signal (e.g., a predefined procedure at the dialysis machine DG1, e.g., a first start-up procedure may act as a trigger signal), the dialysis machine DG1 should prevent the pairing mode from starting. This is a protection functionality. Above all, this ensures that the pairing mode cannot be activated during treatment. This step may be decoupled in time from the subsequent steps and is therefore shown in dashed lines in FIG. 3. Subsequently, the initiation message BROADC1 is sent to the first control entity SI1, which in response sends the first acknowledgement message ACK1 to the dialysis machine DG1, which is answered there with the sending of the second acknowledgment message ACK2 (preferably broadcast message). Only after this predefined handshake protocol, the secure communication connection between the two instances is established.

If several control devices have at the same time tried to register with the dialysis machine DG1 for the purpose of setting up a secure communication connection for controlling the device DG1, then receiving the second confirmation message ACK2 uniquely identifies the control device SG/the server or the first control entity SI1 (which may be a server instance), which has been determined for control. The other devices/instances, which have not received a second acknowledgment message ACK2 within a predefinable period of time, which identifies them as an accepted server instance, are not securely interconnected and can signal this via a corresponding message. Optionally, the securely connected control device SG can output a corresponding message about the interconnection result.

FIG. 4 shows schematically again an overview of the structural architecture of an exemplary embodiment of the invention. The user makes his inputs to control the dialysis machine DG on the remote control device SG. To ensure that the communication channel between the two instances is also secured, the safety protocol is stored and executed in the two integrated circuit components cMC, sMC. Only when the correct execution of the safety protocol has been carried out and the secure communication connection has been established, control commands s can be transmitted from the control device SG to the dialysis machine DG.

In an alternative advantageous embodiment of the invention—as shown in dashed lines in FIG. 4—the user interface GUI can also be arranged outside the control device SG, for example on a mobile terminal of the user, which is connected to the control device SG via wireless communication connection. This makes the control process even more flexible, while at the same time satisfying the required security requirements. The user interface GUI can be part of further automatisms and interactions with the dialysis machine DG. For example, an approximation of a mobile terminal to the dialysis machine DG can be automatically recognized (see U.S. Pat. No. 9,314,207), whereupon the user interface GUI can automatically query the current treatment data and input screens from the control device SG or from the dialysis machine DG and display it on the user interface GUI. (Wireless based proximity detection/location, e.g., via Bluetooth "Google Eddystone"/"Apple iBeacon"). In contrast, however, the communication process is slightly changed. After the GUI has received the "beacon", which also contains the dialysis machine identification DG-ID, the user interface GUI communicates with the control device SG and receives from this the data or sends inputs to the control device SG instead of directly to the dialysis machine DG. This is also shown schematically in FIG. 4. It is also possible for the mobile terminal (for example, a tablet or smartphone) to transmit its identification data to the dialysis machine DG and this then forwards this identification data to the control device SG. The control device SG then sends the respective contents directly to the mobile device.

Figure 5:
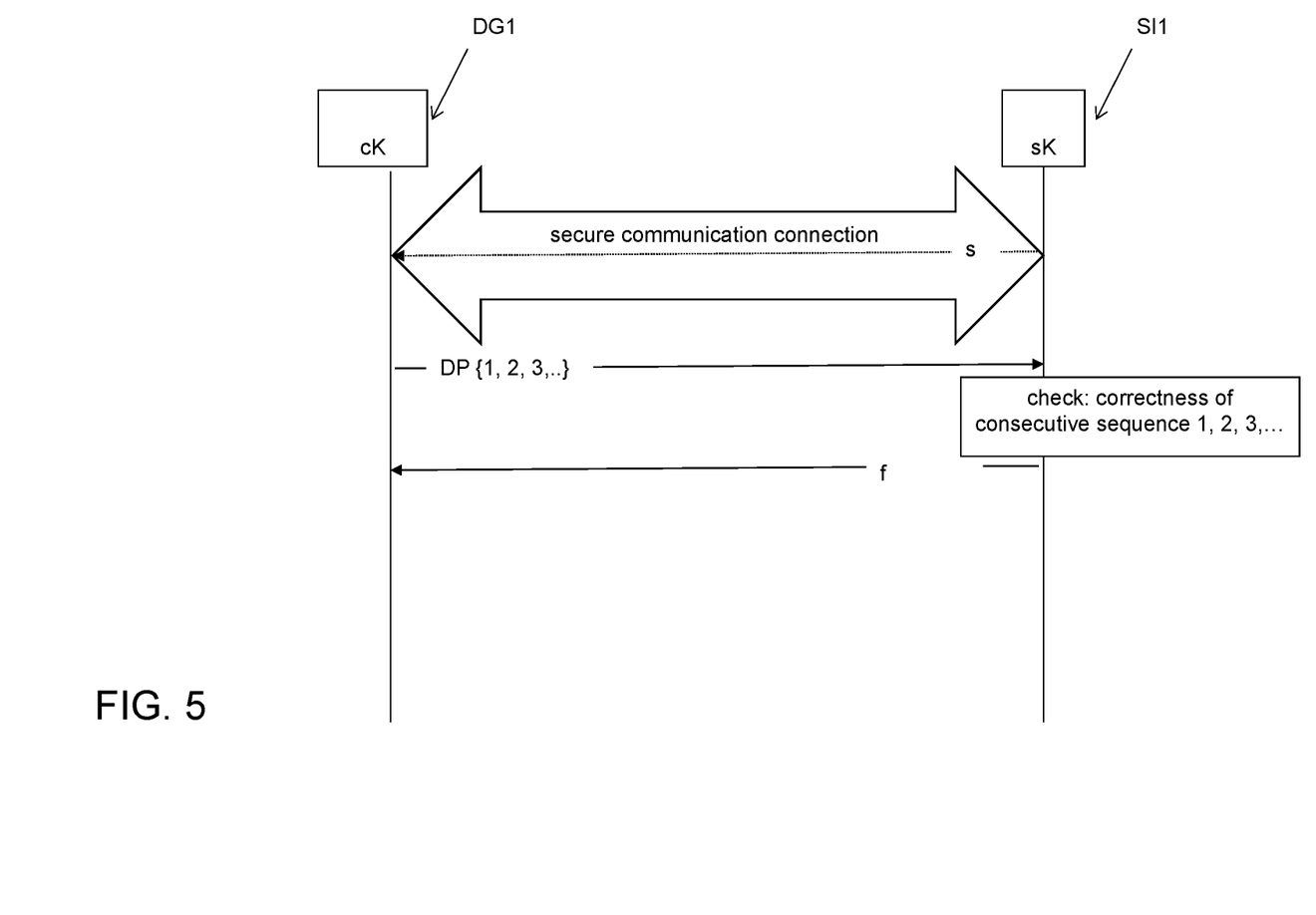
FIG. 5 shows an interaction diagram with a data exchange of signals and messages for an operating method for a protection system for the continuous monitoring of the persisting of a secured communication channel according to an exemplary embodiment of the invention.

Referring to FIG. 5, an operation method for a distributed protection system SchS will be explained in more detail. For this purpose, a secure communication connection is established in advance according to one of the previously described methods (security method). The protection system or the operating method is now used to continuously check whether the established secure communication connection continues to be reliable.

The distributed protection system SchS comprises a client protection system C-SchS implemented on the dialysis machine DG1 and a server protection system S-SchS which can be implemented on a first control entity SI1 of a remote control device SG and in which it is continuously checked whether a secure communication connection between the dialysis machine DG1 and the first control entity SI1 (first aspect of the test) and whether the treatment procedure is correct (second aspect of the test), for example by comparison with a predefinable reference procedure defining that there is no patient at risk condition or by monitoring critical parameters, such as the blood temperature, the conductivity and thus indirectly the composition of the dialysate, freedom from air in the extracorporeal blood circulation. The operating procedure can perform the following, automatically executed steps:

On the server protection system S-SchS, a signal exchange-based check is carried out as to whether a secure communication connection between the dialysis machine DG1 and the first control entity SI1 continues and, if YES, at least one enable signal f is sent cyclically to the dialysis machine DG1. If, for example, it is detected between the transmission time point A and the subsequent transmission time point B that the dialysis machine DG1 has transmitted no data, incorrect data, or too little data to the first control entity SI1, the sending of the enable signal f at time B is omitted.

On the part of the client protection system C-SchS, a fully automatic monitoring is carried out as to whether the at least one enable signal f was received within a predefined fault tolerance time (and thus can be regarded as a correct release signal) and if NO, the dialysis machine DG1 is automatically transferred to a secure device state, which does not endanger patient safety. This has the advantage that sometimes errors in the first control entity SI1 and/or a loss or interruption of the data connection between first control entity SI1 and dialysis machine DG1 can be automatically detected in order to initiate the security-relevant measures automatically. The purpose of the server protection system S-SchS is that the respective protection system instance on the control unit SG (or the control entity SI1) monitors the control signals of the operating system, which is also part of the control unit SG, and only sends a further enable signal f to the dialysis machine DG1 if the control signals are correct, so as to confirm the previous data from the operating system part of the control device SG/control entity SI.

Figure 6:
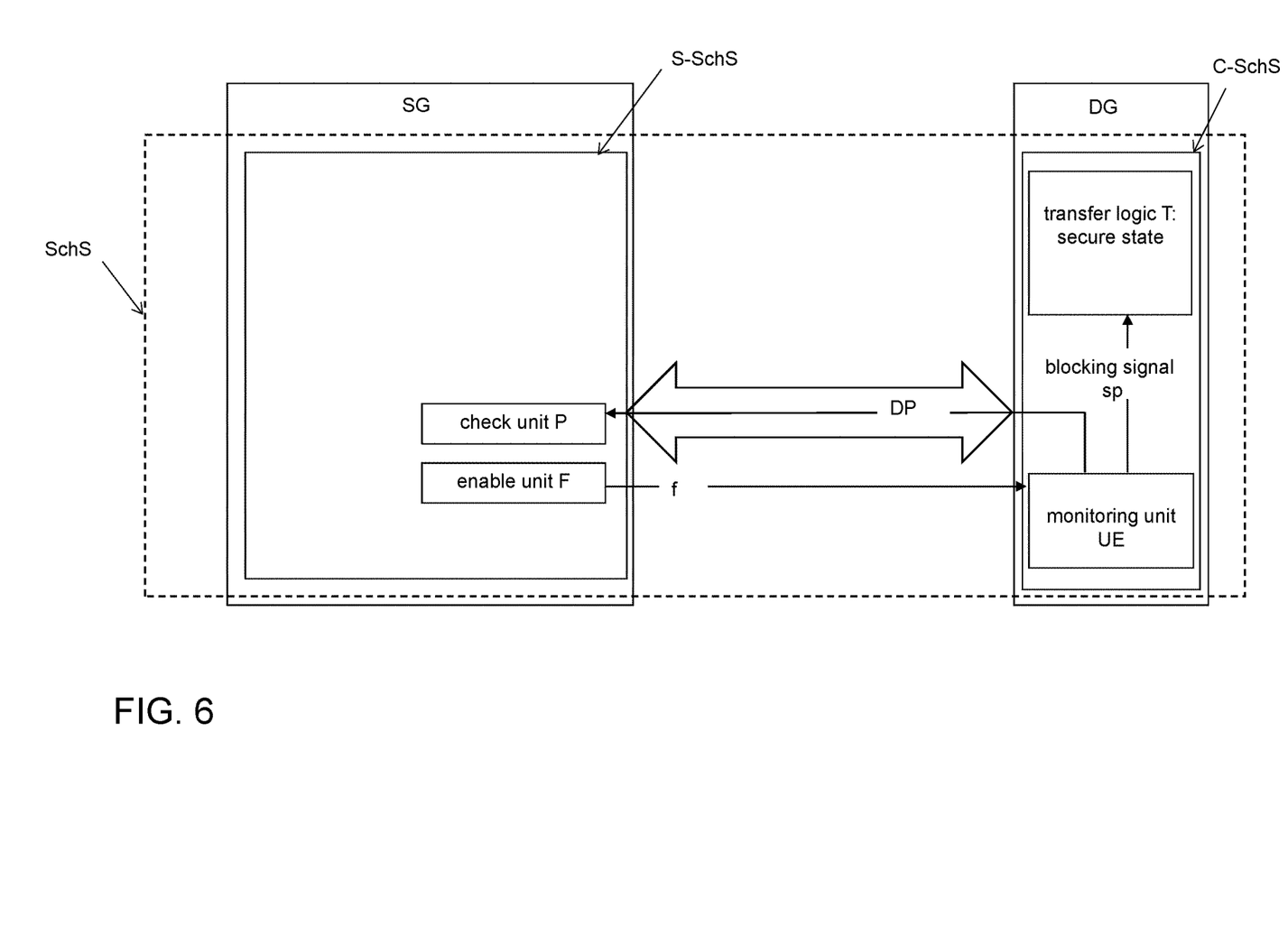
FIG. 6 is a block diagram with electronic units of a distributed protection system according to an exemplary embodiment of the invention.

FIG. 6 shows a block diagram with modules of the distributed protection system SchS according to an exemplary embodiment. Since the protection system SchS is implemented in a distributed manner on multiple physical devices (including control device SG and dialysis machine DG), it is shown in dashed lines in FIG. 6. The server protection system S-SchS comprises the check unit P and the enable unit F, while the client protection system C-SchS comprises the transfer logic T and the monitoring unit UE.

After establishing the secure communication connection via the security method described above, the transmission of status data packets DP by the dialysis machine DG is continuously caused via this connection. These data packets DP can advantageously contain a time stamp, a sequence number and/or sensor signals. The check unit P then checks, on the server protection system S-SchS, whether the data packets have been received in the correct consecutive sequence. For this purpose, either a DESIRED-sequence can be specified or a reference sequence is stored in a central database and used for the comparison. If the check is successful (correct reception alone is not enough), the enable signal f is sent to the client protection system C-SchS. The local monitoring unit UE now serves to continuously monitor whether an enable signal f can be detected. For this purpose, a predetermined test scheme can be stored (for example time-based, approximately every 5 minutes and/or event-based, for example after the occurrence of predeterminable events). If yes, further data packets DP are sent and the operation can be maintained, since it is ensured that the secure communication connection continues and the treatment process is correct, i.e., is carried out without patient risk. Otherwise, a blocking signal sp is generated immediately, which is forwarded to the internal transfer logic T in order to transfer the dialysis machine DG into a secure state. Instead of the blocking signal sp, it can also be provided a further enable signal, which is then not sent, if otherwise the blocking signal sp would be sent. The further enable signal is thus sent if the secure communication connection persists and the treatment process is correct (there is no patient endangerment state). The further enable signal is not sent if there is no secure communication connection or if the treatment procedure is incorrect (or a patient hazardous condition exists). Optionally, in addition, an output on a user interface of the dialysis machine DG and/or the control device SG can take place (for example, as a warning). The output can be made on a hardware module that can be configured in the form of a signal light with appropriate signaling: RED for "interruption of the secure communication connection+transfer to secure device state" and GREEN for "continuation of the secure communication connection+ further operation of the dialysis machine in safe remote control mode."

The dialysis machine DG is controlled by a control entity on the control device SG or an operating system instance. This sends control signals to the dialysis machine DG (for example, to control actuators). Before and/or after, the dialysis machine DG has transmitted data packets (sensor signals, status information on the dialysis machine DG, etc.) to the control entity. All this takes place within a slice/time segment. If the control entity concludes on the basis of the examination of the data packets and if necessary of the control signals from the control instance that there is no patient danger, the control entity sends the further enable signal to the dialysis machine DG. For example, the control entity may evaluate the blood temperature from the data packets from the dialysis machine DG to determine that it exceeds the permissible value of, for example, 41° C., so that the control instance does not send an enable signal. Or the control entity determines that an operating system instance does not comply with its execution order and that the control signals are partly missing or transmitted in the wrong order to the device DG, so that likewise no further enable signal is sent. In general, it is possible that the protection system which performs the second part of the test (process sequence correct, for example blood temperature below the limit value) remains in the dialysis machine DG and only the operating system is implemented in the external control device SG. This can ensure a higher level of security.

Exemplary embodiments of the present application provide a protection concept with a security method and an operating method and corresponding electronic units to enable a secure remote control of a medical device. In this case, the protection is continuously checked to automatically bring the device to be controlled in a secure state as soon as it is detected that the secure communication connection is no longer or has been temporarily or completely interrupted or is faulty. By executing the safety protocol as a handshake protocol, the communication connection is advantageously repeatedly secured.

The description of the invention and the embodiments are generally to be seen as non-limiting in regards to a certain physical realization of the invention. Features described and shown in connection with the individual embodiments of the invention can be configured in different combinations in order to realize their advantageous effects at the same time. It is thus also within the scope of the application to provide in addition to or instead of the network NW between the dialysis machine DG and the control device SG other interfaces or connections. It will be appreciated that exemplary embodiments of the invention can not only be used for dialysis machines (e.g., for a hemodialysis machine or a peritoneal dialysis machine), but also for other medical devices that can be controlled via a remote control device SG in a secured way in accordance with the principles discussed herein.

Furthermore, the components of the dialysis machine DG and the control device SG, such as the user interface GUI, can be realized in a distributed manner across several physical products.

It will be appreciated that the execution of the various machine-implemented processes and steps described herein may occur via the execution, by one or more respective processors, of processor-executable instructions stored on a tangible, non-transitory computer-readable medium, such as random access memory (RAM), read-only memory (ROM), programmable read-only memory (PROM), and/or another electronic memory mechanism. Thus, for example, operations performed by a medical device or a computation device as discussed herein may be carried out according to instructions stored on and/or applications installed on one or more respective computing devices.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A control device for establishing a secure communication connection for controlling at least one medical device, wherein the control device is remote from the at least one medical device, and wherein the control device comprises:

at least one control entity assigned to control the at least one medical device;
a server-side communication device for communication with the at least one medical device; and
an integrated circuit component configured to implement a protocol for establishing the secure communication connection for controlling the at least one medical device, wherein the protocol includes exchanging identification messages for one-to-one identification between a respective medical device and a respective control instance on the control device;
wherein the protocol further includes:
the control device evaluating whether a second acknowledgement message has been received within a predefined timeout period in response to a first acknowledgement message sent by the control device; and
based on determining that the second acknowledgement message has been received within the predefined timeout period in response to the first acknowledgement message sent by the control device, issuing an interconnection message on the control device.

2. The control device according to claim 1, wherein the at least one medical device includes at least one dialysis machine.

3. The control device according to claim 1, wherein the protocol is activated in response to the control device receiving an initiation message.

4. The control device according to claim 1, wherein the control device further comprises a user interface and/or is in communication with a separate user interface, wherein the user interface is configured for detecting control signals for controlling the at least one medical device and/or for outputting status data of the at least one medical device.

5. The control device according to claim 1, wherein the protocol further includes:
based on determining that a respective second acknowledgement message has not been received within the predefined timeout period in response to a respective first acknowledgement message sent by the control device, issuing a miscommunication message on the control device.

6. A medical device, comprising:
a client-side communication device configured for communication with a server-side communication device of a control device; and
an integrated circuit component configured to implement a protocol for establishing a secure communication connection to the control device, and wherein the protocol includes exchanging messages with a respective control entity on the control device for one-to-one identification between the medical device and the respective control entity, wherein the respective control entity is configured for dedicated control of the medical device;
wherein the protocol further includes:
the control device evaluating whether a second acknowledgement message has been received within a predefined timeout period in response to a first acknowledgement message sent by the control device; and
based on determining that the second acknowledgement message has not been received within the predefined timeout period in response to the first acknowledgement message sent by the control device, issuing a miscommunication message on the control device.

7. The medical device according to claim 6, wherein the medical device is a dialysis machine and further comprises at least one fluid handling component.

8. A medical system, comprising:
at least one medical device configured to communicate with a control device via at least one network; and
the control device, wherein the control device is remote from the at least one medical device, and wherein the control device is configured to communicate with and control the at least one medical device via the at least one network;
wherein the at least one medical device and the control device are configured to implement a protocol for establishing a secure communication connection between the at least one medical device and the control device, wherein the protocol includes a respective medical device exchanging messages with a respective control entity on the control device for one-to-one identification between the respective medical device and the respective control entity, wherein the respective control entity is configured for dedicated control of the respective medical device;
wherein the protocol further includes:
the control device evaluating whether a second acknowledgement message has been received within a predefined timeout period in response to a first acknowledgement message sent by the control device; and
based on determining that the second acknowledgement message has been received within the predefined timeout period in response to the first acknowledgement message sent by the control device, issuing an interconnection message on the control device.

9. The medical system according to claim 8, wherein the at least one medical device includes at least one dialysis machine.

10. The medical system according to claim 8, wherein a user interface of the control device is formed on a separate device outside the control device, wherein the separate device is configured to communicate with the control device.

11. The medical system according to claim 10, wherein the separate device is configured to communicate with the control device via a medical device based on a position sensor detecting that the separate device is within a spatial proximity relative to the medical device.

12. A method for establishing a secure communication connection between at least one medical device and a control device, wherein the control device comprises at least one control entity for controlling the at least one medical device, wherein the method comprises:
the control device and the at least one medical device implementing a protocol for establishing a secure communication connection for controlling the at least one medical device, wherein the protocol includes a respective medical device exchanging messages with a respective control entity on the control device for one-to-one identification between the respective medical device and the respective control entity;
wherein the protocol further includes:
the control device evaluating whether a second acknowledgement message has been received within a predefined timeout period in response to a first acknowledgement message sent by the control device; and
based on determining that the second acknowledgement message has been received within the predefined timeout period in response to the first acknowledgement message sent by the control device, issuing an interconnection message on the control device.

13. The method according to claim 12, wherein the at least one medical device includes at least one dialysis machine.

14. The method according to claim 12, further comprising:
   determining a trigger signal on the at least one medical device to trigger execution of the protocol.

15. The method according to claim 12, wherein the protocol includes:
   the respective medical device sending an initiation message with a unique device identification for the respective medical device to the control device;
   the control device sending the first acknowledgment message to the respective medical device with an identification of the respective control entity in response to the initiation message; and
   the respective medical device sending the second acknowledgement message in response to the first acknowledgement message to the control device.

16. The method according to claim 15, further comprising:
   configuring the control device in response to the received initiation message.

17. The method according to claim 15, wherein a plurality of control entities are formed on the control device, and wherein the initiation message is a broadcast message broadcasted to all of the plurality of control entities.

18. The method according to claim 15, wherein a plurality of control entities are formed on a plurality of control devices in a network, and wherein the initiation message is a broadcast message broadcasted to all of the plurality of control entities.

19. The method according to claim 15, wherein the initiation message comprises an equipment code and/or calibration data representing technical equipment of the respective medical device.

20. The method according to claim 12, wherein after execution of the protocol, an interconnection result is displayed on a user interface of the control device and/or a user interface of the at least one medical device.

21. The method according to claim 12, wherein after execution of the protocol, an interconnection result is signaled via activation of a hardware component.

22. The method according to claim 12, wherein the protocol further includes:
   based on determining that a respective second acknowledgement message has not been received within the predefined timeout period in response to a respective first acknowledgement message sent by the control device, issuing a miscommunication message on the control device.

23. A control device for establishing a secure communication connection for controlling at least one medical device, wherein the control device is remote from the at least one medical device, and wherein the control device comprises:
   at least one control entity assigned to control the at least one medical device;
   a server-side communication device for communication with the at least one medical device; and
   an integrated circuit component configured to implement a protocol for establishing the secure communication connection for controlling the at least one medical device, wherein the protocol includes exchanging identification messages for one-to-one identification between a respective medical device and a respective control instance on the control device;
   wherein the protocol further includes:
   the control device evaluating whether a second acknowledgement message has been received within a predefined timeout period in response to a first acknowledgement message sent by the control device; and
   based on determining that the second acknowledgement message has not been received within the predefined timeout period in response to the first acknowledgement message sent by the control device, issuing a miscommunication message on the control device.

* * * * *